(12) United States Patent
Voelkel

(10) Patent No.: US 10,896,607 B2
(45) Date of Patent: Jan. 19, 2021

(54) METHOD AND APPARATUS FOR OPERATING A DRIVER ASSISTANCE SYSTEM, DRIVER ASSISTANCE SYSTEM

(71) Applicant: Robert Bosch GmbH, Stuttgart (DE)

(72) Inventor: Andreas Voelkel, Ispringen (DE)

(73) Assignee: Robert Bosch GmbH, Stuttgart (DE)

( * ) Notice: Subject to any disclaimer, the term of this patent is extended or adjusted under 35 U.S.C. 154(b) by 553 days.

(21) Appl. No.: 15/377,632

(22) Filed: Dec. 13, 2016

(65) Prior Publication Data
US 2017/0178509 A1    Jun. 22, 2017

(30) Foreign Application Priority Data

Dec. 16, 2015  (DE) .................... 10 2015 225 384
May 17, 2016  (DE) .................... 10 2016 208 405

(51) Int. Cl.
| | | |
|---|---|---|
| G08G 1/0962 | (2006.01) | |
| G08G 1/0968 | (2006.01) | |
| G06K 9/00 | (2006.01) | |
| A61B 5/18 | (2006.01) | |
| B60Q 9/00 | (2006.01) | |
| G01C 21/36 | (2006.01) | |

(52) U.S. Cl.
CPC ......... *G08G 1/096855* (2013.01); *A61B 5/18* (2013.01); *B60Q 9/00* (2013.01); *G01C 21/3697* (2013.01); *G06K 9/00845* (2013.01); *G08G 1/0962* (2013.01)

(58) Field of Classification Search
CPC ...... G08G 1/096855; A61B 5/18; B60Q 9/00; G01C 21/3697
USPC ...................................... 340/568.1
See application file for complete search history.

(56) References Cited

U.S. PATENT DOCUMENTS

| | | | |
|---|---|---|---|
| 2010/0007479 A1* | 1/2010 | Smith ............... | B60W 50/14 340/436 |
| 2012/0099170 A1* | 4/2012 | Shikii ............... | G02B 27/0103 359/3 |
| 2015/0094899 A1* | 4/2015 | Hackenberg ....... | B60W 50/082 701/23 |
| 2015/0194035 A1* | 7/2015 | Akiva ............... | H04N 7/183 340/575 |
| 2016/0202700 A1* | 7/2016 | Sprigg .............. | G05D 1/0088 701/23 |

* cited by examiner

*Primary Examiner* — Hai Phan
*Assistant Examiner* — Anthony D Afrifa-Kyei
(74) *Attorney, Agent, or Firm* — Norton Rose Fulbright US LLP; Gerard Messina

(57) ABSTRACT

A method for operating a driver assistance system for a motor vehicle, a viewing direction of a driver of the motor vehicle being monitored and compared to at least one setpoint value. The at least one setpoint value is determined as a function of the course of a route, and an attention value is determined for the driver as a function of the comparison.

15 Claims, 2 Drawing Sheets

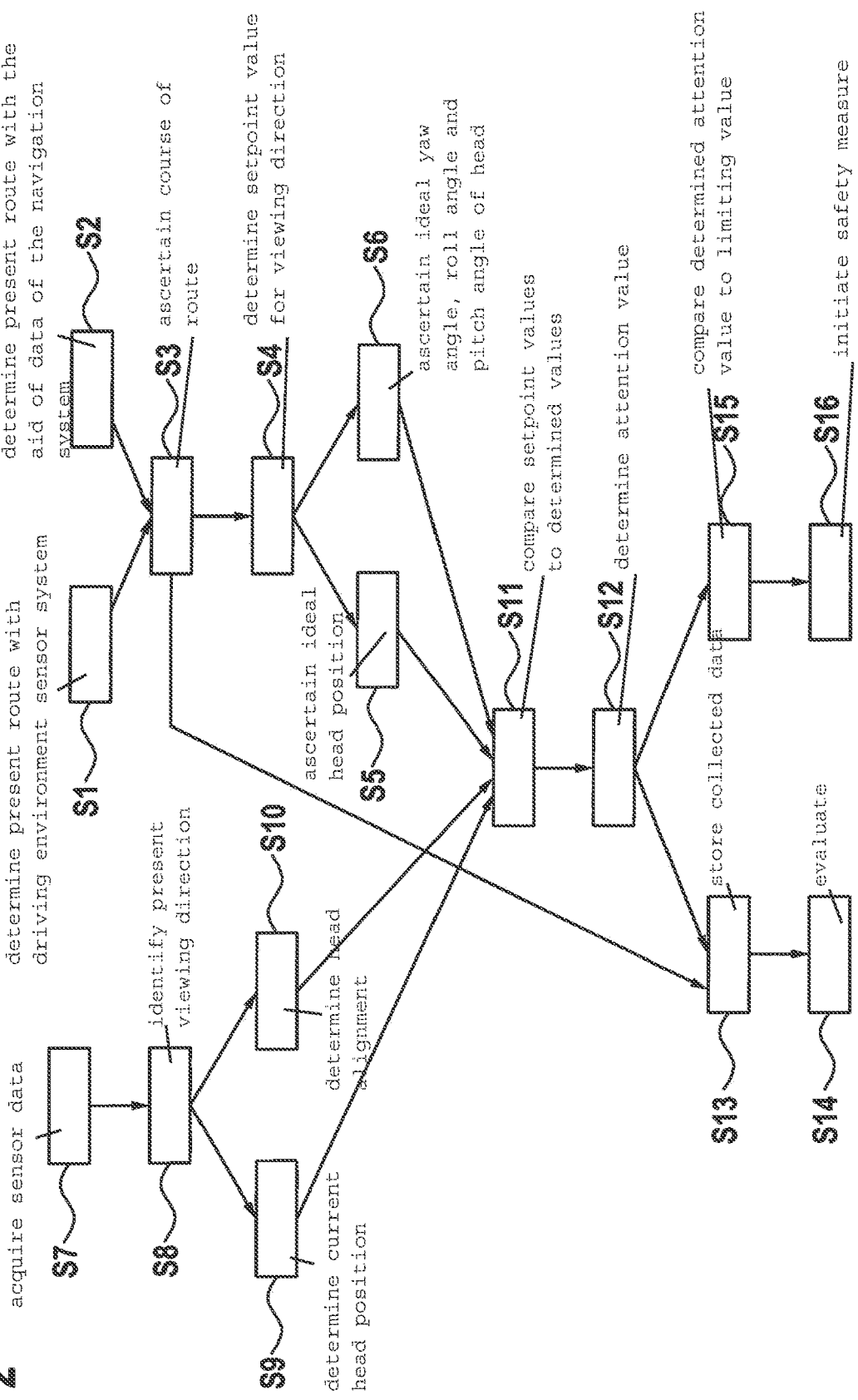

METHOD AND APPARATUS FOR OPERATING A DRIVER ASSISTANCE SYSTEM, DRIVER ASSISTANCE SYSTEM

CROSS REFERENCE

The present application claims the benefit under 35 U.S.C. § 119 of German Patent Application Nos. DE 102015225384.8 filed on Dec. 16, 2015, and DE 102016208405.4 filed on May 17, 2016, which are each expressly incorporated herein by reference in its entirety.

FIELD

The present invention relates to a method for operating a driver assistance system, an instantaneous viewing direction of a driver of the vehicle being monitored and compared to at least one setpoint value.

The present invention also relates to an apparatus for operating a driver assistance system, the apparatus having a sensor device for detecting the instantaneous viewing direction of the driver of the vehicle. In addition, the present invention relates to a corresponding driver assistance system for a motor vehicle.

BACKGROUND INFORMATION

For the driving of vehicles, especially motor vehicles of any kind, it is important that the driver correctly direct his gaze or correctly orient his eyes, so as to be able to safely guide the vehicle. Especially when turning into a curve, the driver therefore does not look straight ahead, but rather into the curve, thus, turns his gaze toward the curve.

Conventional driver assistance systems monitor the viewing direction, especially the alignment and/or position of the head of a driver during operation of the motor vehicle, using suitable sensors. For example, this is used to recognize drowsiness symptoms of the driver.

SUMMARY

An example method in accordance with the present invention may have the advantage that the attentiveness of the driver is monitored, especially independently of states of drowsiness of the driver, to thereby be able to purposefully increase road-traffic safety. This is achieved according to the present invention by determining the at least one setpoint value as a function of the course of a route, and determining an attention value for the driver as a function of the comparison. Thus, the invention provides that the attention of the driver is ascertained as a function of the course of the route and the viewing direction of the driver. To that end, at least one setpoint value is ascertained for the viewing direction of the driver as a function of the course of the route, especially based on the respective position of the vehicle on the route. If the ascertained viewing direction does not agree with the setpoint value, it may then be inferred in an easy manner that the driver is not attentive, and in particular, is not following the course of the route with his eye. If the attention value reaches a critical value, then preferably an intervention is carried out in the operating behavior of the vehicle, or at the least, the driver is given warning of his inappropriate behavior.

Preferably, the attention value is reduced if the viewing direction differs from the respective setpoint value at least beyond a specifiable period of time. With increasing deviation of the viewing direction from the setpoint value, a decreased or reduced attention of the driver is therefore inferred. The more frequently the driver does not follow the course of the route with his eye or the longer he does not direct his gaze toward the route, the lower his attention is deemed to be. In this way, in the event of small or short-duration deviations of the viewing direction of the driver from the setpoint value, he is not immediately judged to be inattentive. Rather, it is allowed to the driver that he may be distracted briefly. In this context, the time and/or deviation from the setpoint values is/are preferably assessed differently depending on the routing of the road. At the same time, in particular, the weighting is also carried out as a function of the current driving speed of the vehicle, in order to give consideration to the specific traffic situation.

It is especially preferred that the attention value is reduced as a function of the magnitude of the deviations. Thus, the later the driver turns his eye toward the course of the route or the further he turns his gaze away from the course of the route, the more the attention value is reduced, so that it more quickly reaches a critical limit. This ensures that in response to particularly great deviations from the setpoint value(s), the lack of attention on the part of the driver is recognized quickly.

Furthermore, preferably in each case an attention value is ascertained for predetermined route sections or locations on the route. Thus, multiple attention values may be ascertained during the course of operation. Preferably, the various attention values are stored, so as afterwards to be able to evaluate the behavior of the driver on the traversed route. In particular, the method is therefore also used to train the driver if he repeatedly travels on the route. Thus, attention values which were ascertained at the same spot on the route at different times are preferably compared to each other in order to discern a learning process of the driver. Consequently, the method is also especially suitable for driving instruction, both in the case of motor vehicles and in the case of two-wheel vehicles, where a driving instructor himself is unable to recognize whether or not the eye of the driver is directed correctly.

Furthermore, preferably the course of the route is ascertained with the aid of a driving environment sensor system of the motor vehicle. Consequently, the course of the route is ascertained from the perspective of the vehicle itself, so that a direct comparison may be made with the viewing direction of the driver in order to determine the respective attention value. In particular, a camera sensor system is used as driving environment sensor system, that optically monitors the surroundings of the vehicle, in doing so, the course, or the possible course, especially the most probable course of the route being ascertained by image evaluation, in order to determine the setpoint value(s).

Preferably it is also provided that additionally or alternatively, the course of the route is ascertained with the aid of data of a satellite-based navigation system. Especially in the case of active navigation, thus, when the destination is known and the route is predetermined by the navigation system, the most probable course of the route is determinable in an easy manner. An ideal viewing direction of the driver for safe operation of the vehicle is determinable or calculable as a function of the course of the route and the position of the vehicle on the route, and the setpoint value(s) may be determined based on the ideal viewing direction.

In addition, preferably the attention value is compared to a limiting value, and if the attention value drops below the limiting value, at least one safety measure is initiated. The attention value is thus compared continuously to the limiting value, in order thereupon to recognize whether the attention of the driver has reached a critical state. Especially because the attention value is reduced depending on the magnitude of the deviation, the limiting value is undershot earlier or later as a function of the magnitude of the deviation, and the safety measure for ensuring a safe vehicle operation is initiated accordingly. In addition, preferably the attention value is increased if, in the further course, the deviation of the viewing direction from the setpoint value(s) decreases, and in particular, drops below a minimum deviation, so that a brief lack of attention on the part of the driver may be offset, in order to avoid the premature initiation of a safety measure.

In particular, a warning message is output to the driver as safety measure. The warning message especially is output visually and/or acoustically, in order to alert the driver that he should increase his attention and, in particular, should turn his eye in a certain direction. Notably, the warning message is output in such a way that, in addition, the driver is given an indication of the direction in which he should direct his eye. In the case of a visual warning message, this may be achieved simply by arrows or the location at which the warning message is output visually. In the case of an acoustic warning message, this may likewise be achieved by outputting the warning message at a specific location in the motor vehicle, e.g., to the right or to the left of the driver. The warning message could also contain the indication of the viewing direction itself, by outputting to the driver a voice instruction that contains an indication of direction.

According to one preferred further refinement of the present invention, to monitor the viewing direction, a position and/or an alignment of the head of the driver is/are ascertained or detected. In general, it may be provided, and according to a first exemplary embodiment, is also provided, that the viewing direction is ascertained by an image evaluation of the sensor device, in which the eyes of the driver are detected and, as a function of the position and alignment of the eyes, the viewing direction and the viewing position, thus, the position of the eyes in the driver's cockpit, are determined, and in this manner, a viewing direction is ascertained. This is possible with any sensor device designed to detect the orientation of the eyes of the driver. Suitable sensor devices are already well-known. According to a second specific embodiment, preferably the viewing direction is determined as a function of the position and/or alignment of the head of the driver. It is thereby possible to dispense with a costly evaluation of the position and alignment of the eyes of the driver. This facilitates the monitoring of the viewing direction and, in particular, makes it possible to monitor the viewing direction even when the driver, especially his eyes, cannot be recognized or detected by the sensor device. For example, this is the case when the method described is used for a two-wheel vehicle or motorcycle, where the rider is obligated to wear a helmet whose visor conceals the eyes, thereby making it difficult to detect them. By monitoring the head position and the head alignment, it is therefore possible to indirectly infer the viewing direction or gaze direction of the rider. In particular, a pitch angle, a yaw angle and a roll angle of the head of the rider are detected to determine the head alignment.

Furthermore, as setpoint values, preferably an ideal head position, an ideal head pitch angle, head yaw angle and/or head roll angle are determined for the head of the driver/rider as a function of the instantaneous position of the vehicle on the route. An ideal viewing direction is thereby obtained for the driver/rider as a function of the instantaneous position of the vehicle on the route.

An example apparatus in accordance with the present invention includes a specially adapted control unit, which implements the method according to the present invention when used as intended. The advantages already indicated are thereby obtained. Further advantages and preferred features are derived especially from the previous description as well as from the claims.

An example vehicle in accordance with the present invention includes the apparatus according to the present invention. The advantages discussed above may be obtained here, as well.

The present invention is explained in greater detail below with reference to the figures.

BRIEF DESCRIPTION OF THE DRAWINGS

FIG. 2 shows a diagram to clarify an advantageous method for operating the vehicle.

DETAILED DESCRIPTION OF EXAMPLE EMBODIMENTS

Figure 1:
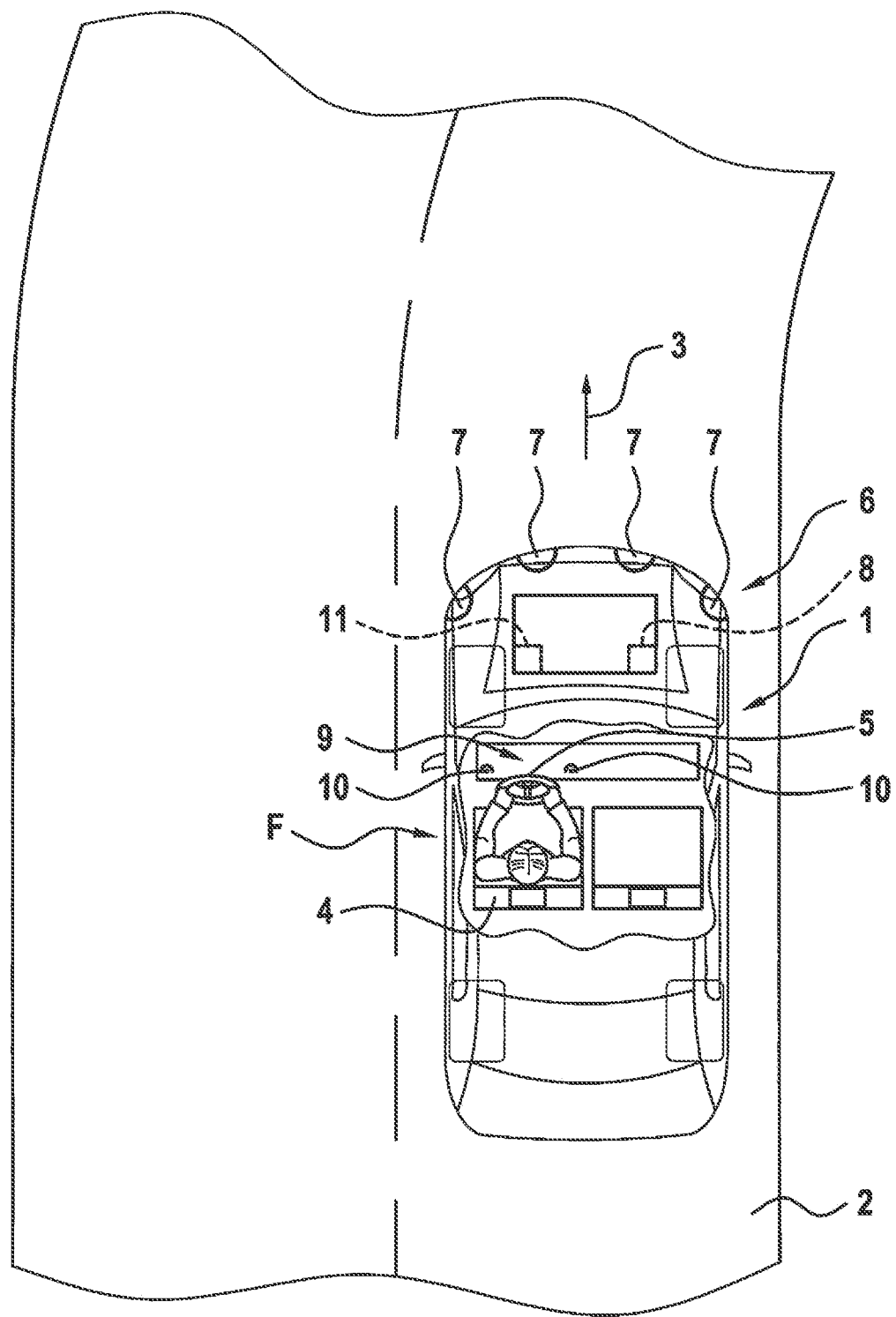
FIG. 1 shows a vehicle in a simplified top view.

FIG. 1 shows a simplified top view of a vehicle 1 in the form of a motor vehicle, which is located on a roadway 2 and, according to arrow 3, is moving in the direction of the route predefined by roadway 2. Motor vehicle 1 is driven by a driver F who is seated in a driver's seat 4 and, in particular, is steering motor vehicle 1 with the aid of a steering wheel 5, together with pedals (not shown here).

Motor vehicle 1 also has a driving environment sensor system 6 having a plurality of sensors 7 disposed especially at the front end, which take the form of camera sensors, ultrasonic sensors or the like, in order to continuously monitor the surroundings, especially in the direction of travel of motor vehicle 1. Additionally or alternatively, motor vehicle 1 has a satellite-based navigation system 8 which determines the instantaneous position of motor vehicle 1 on a virtual map, and, if desired, is used for route guidance and for calculating an optimal route for motor vehicle 1, in order to reach a desired destination.

Moreover, motor vehicle 1 has a sensor device 9 that has one or more, in the present case two sensors 10, preferably in the form of camera sensors. Sensors 10 are assigned to the driver in such a way or are aligned with the driver in such a way that, in particular, they detect the head of the driver during operation of motor vehicle 1. Sensor device 9 is designed in particular to detect and evaluate the alignment of the head in terms of its pitch angle, yaw angle and roll angle, as well as the position of the head in the driver's cockpit. In addition, sensor device 9 is designed especially to ascertain a gaze direction of the eyes of the driver by image evaluation.

With the aid of driving environment sensor system 6 and/or using data of navigation system 8, to which a predefined route is already possibly known, a control unit 11 monitors the course of the route to be driven over by motor vehicle 1. From this data, control unit 11 first of all determines the most likely route for motor vehicle 1. In the simplest case, the route predetermined by navigation system 8 is used as the most likely route. As a function of the ascertained route and the position of motor vehicle 1 on this route, one or more setpoint values is/are determined for a viewing direction of the driver of motor vehicle 1. In particular, setpoint values are ascertained for the head pitch angle, head yaw angle and/or head roll angle, as well as for the position of the head in the driver's cockpit, from which an ideal viewing direction is obtained that ensures the greatest possible safety when driving motor vehicle 1 on the given route. Sensor device 9, control unit 11 and driving environment sensor system 6 and/or navigation system 8 together form a driver assistance system.

FIG. 2, in a simplified flowchart, shows an advantageous method for operating the driver assistance system. As already described, in steps S1 and/or S2, first of all, the course of the present route is determined with the aid of the data of driving environment sensor system 9 (step S1) and/or with the aid of the data of the navigation system (step S2) and supplied to the control unit, which, in a step S3, ascertains the course of the route and in a following step S4, as a function of the course of the route and the position of vehicle 1, especially with the aid of a model for the ideal guidance of the eyes, determines a setpoint value for the viewing direction of the driver. From the determined viewing direction, in a step S5, control unit 11 furthermore ascertains the ideal head position, as well as, in a step S6, the ideal yaw angle, roll angle and pitch angle of the head of the driver, by which it is possible to achieve the ideal viewing direction.

In a step S7, the data of sensor device 9 is acquired as previously described, and from it, in a step S8, the present viewing direction of the driver is identified. To that end, in particular, the current head position is determined in a step S9, and the head alignment, namely, the yaw angle, roll angle and pitch angle of the head of the driver, is determined in a step S10.

In a step S11, the setpoint values are compared to the instantaneously determined values, in order to identify deviations of the actual values from the setpoint values.

In addition, in a step S12, an attention value of the driver is determined as a function of the deviation of the actual values (actual viewing direction) from the setpoint values (ideal viewing direction). In so doing, the extent to which the gaze of the driver deviates from the ideal viewing direction is identified, so that the attention value reflects a quality of the eye guidance.

If the viewing direction matches with the ideal viewing direction, or rather, if the actual values agree or almost agree with the setpoint values, then preferably, the attention value is increased, while if the actual values deviate from the setpoint values, then the attention value is reduced. In so doing, the reduction of the attention value is determined especially as a function of the magnitude of the deviation and the length of the deviation in time.

In the process, the attention value is either reduced or increased continuously as a function of the behavior of the driver, or in each case an attention value is stored or generated for multiple road sections and/or locations on the route.

The data thus acquired is used either to permit a subsequent evaluation of the behavior of the driver, or to instantaneously initiate safety measures in order to ensure the safe guidance of the motor vehicle.

In the first case, in a step S13, the collected data is stored, especially in a nonvolatile memory, and evaluated at a later time in a step S14 in order, for example, to subsequently permit the driver to check his own behavior. The data may also be evaluated by a driving instructor or such, for example, in order to check the behavior of his student.

In the second case, in a step S15, the ascertained attention value(s) is/are compared to a specifiable limiting value. If the attention value drops below the limiting value, then in a step S16, a safety measure is initiated. In particular, the safety measure involves drawing the attention of the driver or a driving instructor to the lack of attention on the part of the driver. The attention is drawn especially by a visual and/or acoustic warning, particularly in motor vehicle 1. A live monitoring of the driver during operation of the vehicle is thereby ensured.

Through the method described here, it is thus ensured that the driver, especially the viewing direction of the driver, is monitored based on the situation, which means on one hand, the driver is able to be trained, and on the other hand, critical driving situations may be avoided. While the present exemplary embodiment is specific to a motor vehicle, naturally, it is possible to carry out the method in the case of a two-wheel vehicle, particularly a motorcycle, as well.

What is claimed is:

1. A method for operating a driver assistance system for a motor vehicle, comprising:
    determining, by a navigation system, a route for the motor vehicle to a predetermined destination;
    ascertaining a position of the motor vehicle on the determined route;
    determining at least one setpoint value based on the determined route and the ascertained position of the motor vehicle on the determined route;
    monitoring a viewing direction of a driver of the motor vehicle;
    comparing the viewing direction to the at least one setpoint value, and an attention value is determined for the driver as a function of the comparison;
    comparing the attention value to a limiting value; and
    outputting to the driver, based on a result of the comparing of the attention value to the limiting value, at least one of acoustic warning and a visual warning;
    wherein the attention value is reduced if the viewing direction deviates from the respective setpoint value at least beyond a specifiable period of time.

2. The method as recited in claim 1, wherein the attention value is reduced as a function of the magnitude of the deviation.

3. A method for operating a driver assistance system for a motor vehicle, comprising:
    determining, by a navigation system, a route for the motor vehicle to a predetermined destination;
    ascertaining a position of the motor vehicle on the determined route;
    determining at least one setpoint value based on the determined route and the ascertained position of the motor vehicle on the determined route;
    monitoring a viewing direction of a driver of the motor vehicle;
    comparing the viewing direction to the at least one setpoint value, and an attention value is determined for the driver as a function of the comparison;
    comparing the attention value to a limiting value; and
    outputting to the driver, based on a result of the comparing of the attention value to the limiting value, at least one of acoustic warning and a visual warning;
    wherein in each case an attention value is ascertained for predetermined route sections or locations on the route.

4. The method as recited in claim 1, wherein the position of the vehicle on the determined route is ascertained with the aid of a driving environment sensor system of the motor vehicle.

5. The method as recited in claim 1, wherein the position of the vehicle on the determined route is ascertained with the aid of data of a satellite-based navigation system.

6. The method as recited in claim 1, wherein at least one of an instantaneous position of a head of the driver, and an alignment of the head is ascertained in order to monitor the viewing direction.

7. The method as recited in claim 1, wherein as setpoint values, at least one of an ideal head position, an ideal head pitch angle, head yaw angle and head roll angle are determined for the head of the driver as a function of an instantaneous position of the vehicle on the route.

8. An apparatus for operating a driver assistance system for a motor vehicle, comprising:
- a navigation system to determine a route for a motor vehicle to a predetermined destination;
- a device to ascertain a position of the motor vehicle on the determined route, the device being at least one of: (i) the navigation system, and (ii) a driving environment sensor system;
- a sensor device to detect a viewing direction of a driver of the vehicle; and
- a specially adapted control unit designed to monitor the viewing direction of a driver of the motor vehicle, and compare the viewing direction to at least one setpoint value, wherein the at least one setpoint value is determined as a function of the determined route and the position of the motor vehicle on the determined route, and an attention value is determined for the driver as a function of the comparison;
- wherein the specially adapted control unit is designed to compare the attention value to a limiting value, and to output to the driver, based on a result of the comparison of the attention value to the limiting value, at least one of acoustic warning and a visual warning;
- wherein the attention value is reduced if the viewing direction deviates from the respective setpoint value at least beyond a specifiable period of time.

9. A driver assistance system for a motor vehicle, comprising:
- an apparatus for operating a driver assistance system for a motor vehicle, the apparatus including a navigation system to determine a route for a motor vehicle to a predetermined destination, a device to ascertain a position of the motor vehicle on the determined route, the device being at least one of: (i) the navigation system, and (ii) a driving environment sensor system, a sensor device to detect a viewing direction of a driver of the vehicle, and a specially adapted control unit designed to monitor the viewing direction of a driver of the motor vehicle, and compare the viewing direction to at least one setpoint value, wherein the at least one setpoint value is determined as a function of the determined route and the position of the motor vehicle on the determined route, and an attention value is determined for the driver as a function of the comparison; wherein the specially adapted control unit is designed to compare the attention value to a limiting value, and to output to the driver, based on a result of the comparison of the attention value to the limiting value, at least one of acoustic warning and a visual warning;
- wherein the attention value is reduced if the viewing direction deviates from the respective setpoint value at least beyond a specifiable period of time.

10. The method as recited in claim 1, wherein the visual warning is output to the driver, the visual warning being output one of to the left or to the right of the driver.

11. The method as recited in claim 1, wherein the visual warning is output to the driver in the form of arrows.

12. The method as recited in claim 1, wherein acoustic warning is output to the driver in the form of a voice instruction.

13. The method as recited in claim 6, wherein the alignment of the head is determined as a function of a detected pitch angle of the head, a detected yaw angle of the head, and a detected roll angle of the head, the viewing direction being determined as a function of the alignment of the head.

14. The method as recited in claim 1, wherein the outputting includes controlling a device of the motor vehicle to output the visual warning to the driver.

15. The method as recited in claim 1, wherein the outputting including controlling a device of the motor vehicle to output the acoustic warning to the driver.

* * * * *